United States Patent [19]
Codella

[11] Patent Number: 5,326,972
[45] Date of Patent: Jul. 5, 1994

[54] DIAMOND-BASED, SELF-SAMPLING INTERNAL REFLECTION ELEMENT FOR ON-LINE ANALYSIS OF MATERIALS IN A RECYCLE STREAM

[75] Inventor: Peter J. Codella, Schenectady, N.Y.

[73] Assignee: General Electric Company, Schenectady, N.Y.

[21] Appl. No.: 37,146

[22] Filed: Mar. 25, 1993

[51] Int. Cl.$^5$ ..................... G01N 21/35; G01N 21/01
[52] U.S. Cl. ................................. 250/339.01; 250/341
[58] Field of Search ................ 356/136, 135; 250/341, 250/339

[56] References Cited

U.S. PATENT DOCUMENTS

| | | | |
|---|---|---|---|
| 5,051,551 | 9/1991 | Doyle | 250/341 |
| 5,185,640 | 2/1993 | Wilks, Jr. et al. | 356/300 |

FOREIGN PATENT DOCUMENTS

| | | | |
|---|---|---|---|
| 55-101848 | 8/1980 | Japan | 250/341 |
| 61-200444 | 9/1986 | Japan | 250/341 |

Primary Examiner—Constantine Hannaher
Attorney, Agent, or Firm—Paul R. Webb, II

[57] ABSTRACT

An element which is used to identify materials, such as, thermoplastics and sort these thermoplastics on a moving conveyor belt. Such structures of this type, generally, employ a diamond knife (or point) for use as an internal reflection element to obtain the mid-infrared spectrum of the material sliced (or punctured) by the knife (or point).

20 Claims, 2 Drawing Sheets

DIAMOND-BASED, SELF-SAMPLING INTERNAL REFLECTION ELEMENT FOR ON-LINE ANALYSIS OF MATERIALS IN A RECYCLE STREAM

BACKGROUND OF THE INVENTION

1. Field of the Invention

This invention relates to an element which is used to identify materials, such as, thermoplastics and sort these thermoplastics on a moving conveyor belt. Such structures of this type, generally, employ a diamond knife (or point) for use as an internal reflection element to obtain the mid-infrared spectrum of the material sliced (or punctured) by the knife (or point).

2. Description of the Related Art

It is highly desirable for recycled engineering thermoplastics to be recompounded to produce new formulations which would be almost identical to the original product. In order for this to be successful, the recycle portion must be pure. While contamination with certain polymers may be acceptable, others would produce catastrophic results. Therefore, the basic problem is how to assure purity of a recycle polymer stream.

All recycle proposals involve the grinding of individual items to produce a polymer form that can be economically conveyed, transported, mixed with other materials, and extruded. Identification of individual items, before grinding, is the most efficient process to guarantee purity.

Infrared spectroscopy provides as ideal method of material identification, but sample presentation presents a formidable problem. Often times, these items are too thick to be transparent, too irregular to yield good contact for conventional attenuated total reflectance (ATR) techniques, and/or too dull to reflect a measurable amount of energy. In addition, many items are coated with paint or a metallized or textured layer which would interfere with surface or reflection techniques.

Infrared spectroscopy has proven to be very useful for the identification of polymers. The usual application of this technology involves obtaining a transmission spectrum of the polymer in question and then comparing the spectrum to a library of similarly obtained spectra.

Another typical application involves the use of ATR techniques, as shown in FIG. 1. In particular, light is directed into a high refractive index optical element 2 along light path 8. As the light bounces off the faces of the optical element 2, a portion of the radiation extends beyond the surface of element 2 and penetrates thermoplastic samples 4 and 6. Samples 4 and 6, typically, are cut into strips approximately $\frac{1}{2} \times 1\frac{3}{4}$ inch. Samples 4 and 6 are mounted and tightened against element 2 with, typically, 15 in.-lbs. of pressure. Each time light ray 8 bounces, some of the radiation extends beyond the face of element 2 as shown in areas 10. These areas 10 of the light are called the evanescent waves 10. As wave 10 extends beyond the face of element 2, wave 10 examines material contacting the surface, namely, samples 4 and 6. In this manner, a spectrum is obtained of a thin section of samples 4 and 6 along the front surface of samples 4 and 6. The thickness examined is from 1-15 microns depending on the material and the refractive index of element 2, the angle of incidence, and the refractive index of samples 4 and 6. Typically, all sample spectra are ratioed against a background spectrum obtained with just element 2.

It is also possible to shorten the process time by comparing conventionally obtained interferograms, instead of, spectra. The problem with this technology is material sampling. In order to get a transmission spectrum, the material must be very thin, usually, on the order of several micrometers to tens of micrometers. The usual way to obtain such a sample involves hot pressing a small sample of the polymer. This is a relatively long and labor intensive process that would be almost impossible to automate on a production line or any conveyor-based process.

In some cases, depending on the thickness of the object, it is possible to obtain mid-to-near infrared spectra without sample preparation. This type of technology has proven useful only for sorting plastic bottles and containers. It is important to note that, in this case, the wall thickness of a typical plastic bottle or container is thin enough to obtain spectra with measurable features, in the near infrared and lower mid-infrared regions, without sample preparation.

In the area of engineering thermoplastics, the majority of recycled pieces are too thick to be transparent to near infrared or infrared radiation. Hence, transmission methods cannot be employed. A technique, based on diffuse reflectance, has been shown to be an effective way to obtain the mid-infrared spectrum for these materials. However, significant sample preparation is required. In particular, a small sample of polymer is removed by abrading with a silicon carbide abrasive paper. The sample, still on the paper as small flakes of polymer, is examined in the diffuse reflectance mode to obtain an infrared spectrum. Again, the spectrum is compared to similarly obtained spectra to identify the material. This technique shows promise for recycle applications only where a single sampling would be required to identify a large number of individual parts. An example of such an application would be the dismantling of a number of identical items where the manufacturer is certain all similar parts were manufactured from the same polymer.

Another technique has been devised to obtain spectrum from a flat, moving sample without contacting the surface. In this case, hot air, directed at a point in the sample, provides localized heating. The resulting infrared emission is collected and analyzed to obtain the spectrum. This technique works well with some samples, but would be expected to present insurmountable problems with the assortment of shapes, sizes, and textures anticipated in a recycle stream of engineering thermoplastics. A more advantageous system, then, would be presented if the optical element were able to avoid the problems associated with thick painted, metallized or textured samples while being able to be employed on a conveyor-based system.

It is apparent from the above that there exists a need in the art for an optical element which is capable of being used on a conveyor-based system, and which at least equals the thermoplastic identification characteristics of the known systems, but which at the same time is capable of identifying thermoplastics which are thick painted, metallized or textured without having to prepare the thermoplastic. It is a purpose of this invention to fulfill this and other needs in the art in a manner more apparent to the skilled artisan once given the following disclosure.

SUMMARY OF THE INVENTION

Generally speaking, this invention fulfills these needs by providing an apparatus for identifying materials, comprising a material to be sampled having first and second sides, an optical element means such that said optical element means is substantially embedded in said first side of said material, and a detection means which is operatively connected to said optical element means such that said detection means produces a light beam which interacts with said optical element and said material to produce a spectrum of said material that is used to identify said material.

In certain preferred embodiments, the material is a thermoplastic material. Also, the element is a diamond-based, self-sampling internal reflection element. Finally, the detection means is a Fourier transform infrared spectrometer.

In another preferred embodiment, the element is used as an internal reflection element to obtain the mid-infrared spectrum material as the element is embedded in the material. In the area of recycled thermoplastics, this device could be used to identify and, thereby sort items on a moving conveyor belt.

The preferred sample identification apparatus, according to this invention, offers the following advantages: excellent sample identification characteristics; good stability; good durability; excellent economy; increased speed of sample identification; and high strength for safety. In fact, in many of the preferred embodiments, these factors of sample identification characteristics, economy and identification speed are optimized to an extent that is considerably higher than heretofore achieved in prior, known material identification devices.

BRIEF DESCRIPTION OF THE DRAWINGS

The above and other features of the present invention which will be more apparent as the description proceeds are best understood by considering the following detailed description in conjunction with the accompanying drawings wherein like character represent like parts throughout the several views and in which.

DETAILED DESCRIPTION OF THE INVENTION

Figure 1:
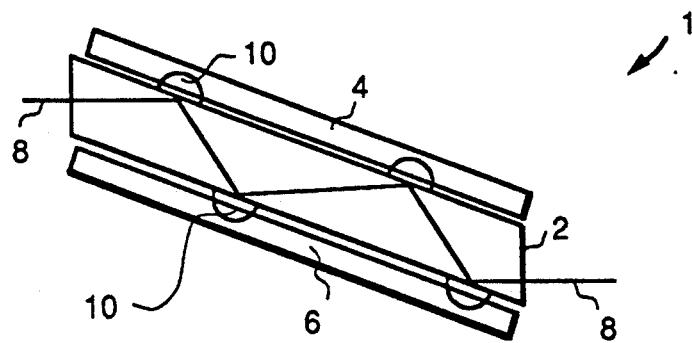
FIG. 1 is a schematic illustration of a conventional sample characterization technique using attenuated total reflectance (ATR), according to the prior art.

As discussed earlier, FIG. 1 illustrates a typical attenuated total reflectance (ATR) apparatus 1. Briefly, during the operation of apparatus 1, light is directed into optical element 2 at one end along reflection beam 8 and exits out the other end of element 2. In between, light bounces back and forth. Each time that the light bounces, some of the radiation extends beyond the face of element 2 (areas 10). This portion of light is called evanescent wave 10. As it extends beyond the face of element 2, wave 10 examines the material of samples 4 and 6 contacting the surface of element 2. In this manner spectra are obtain of a thin section along the front of samples 4 and 6. The thickness examined is from 1-15 microns depending upon the material and refractive index of element 2, the angle of incidence, and the refractive index of samples 4 and 6. All sample spectra are ratioed against background spectra obtained with only element 2.

Figure 2:
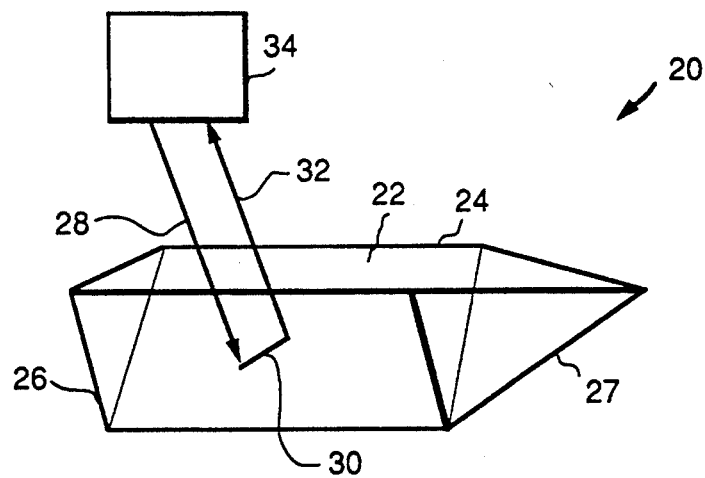
FIG. 2 is a schematic illustration of a diamond-based, self-sampling internal reflection element, according to the present invention.

FIG. 2 illustrates diamond-based, self-sampling internal reflection knife edge element 20. Element 20 includes, in part, a diamond or diamond-like material having faces 22, 24, 26, leading edge 27 and light source/detector 34. Light source/detector 34, preferably, includes a light source, a Fourier transform infrared spectrometer and a detector. It is to be understood that a dispersion spectrometer or a band-pass infrared detector can be used instead of a Fourier transform infrared spectrometer. As can be seen from FIG. 2, a light beam 28 from light source/detector 34 travelling through element 20 first impinges upon face 22, is reflected by face 26 along line 30, reflects off face 24 and exits face 22 along line 32.

Figure 3:
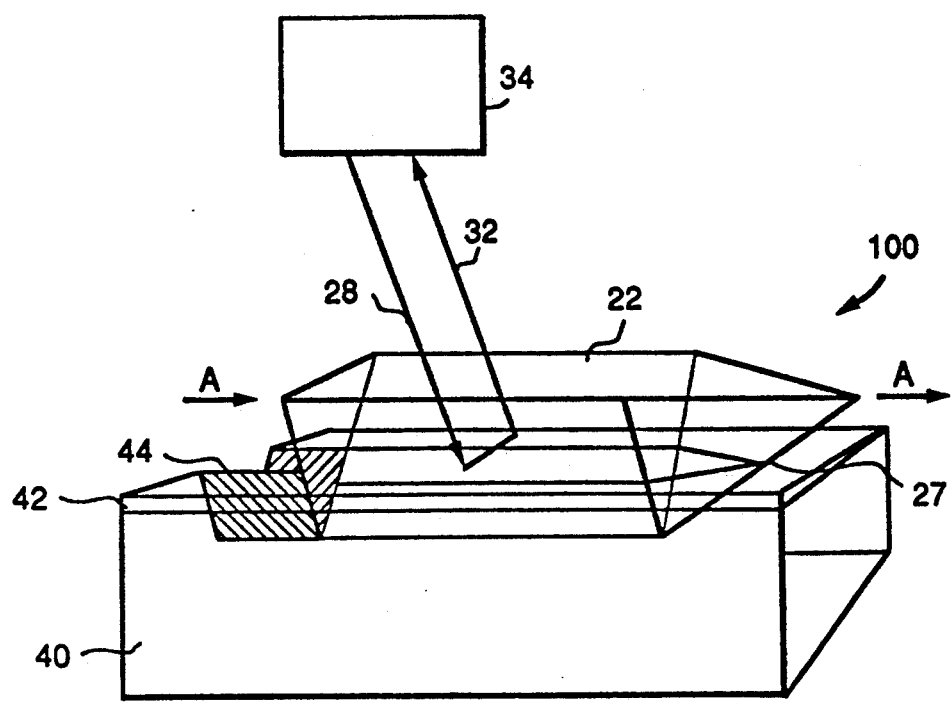
FIG. 3 is a schematic illustration showing how the diamond-based, self-sampling internal reflection element operates, according to the present invention.

During the operation of element 20, element 20 is embedded in sample 40 (FIG. 3). Sample 40, typically, includes a coating 42 which may be metallized, painted, and/or textured. As element 20 plows through sample 40 along the direction of arrow A, a conventional Fourier transform infrared spectrometer located within light source/detector 34 produces light beam 28. Light beam 28, as discussed earlier, interacts with element 20 and exits element 20 along line 32. As element 20 plows through sample 40, a trough 44 is produced in sample 40. Preferably, this trough is only deep enough to extend through painted, metallized, and/or texturized area 42 such that the area that will be examined will be only sample 40 and not area 42. It is to be understood that the light 28 can come from a conventional separate light source (not shown), interact with optical element 20 and sample 40, enter the Fourier transform infrared spectrometer and go to a detector or the light beam 28 can come from the Fourier transform infrared spectrometer, interact with optical element 20 and sample 40, and enter the detector.

Element 20 serves two purposes. First, element 20 will provide a means of penetrating sample 40, thereby sampling the material in the interior of sample 40, which by virtue of painting, metallization, or texturing, may be different from the surface material 42. Second, functioning as an internal reflection element, the element 20 would be used to internally reflect the infrared beam to sample material 40 and return the spectral information to the Fourier transform infrared spectrometer for analysis. A comparison of the infrared spectrum, generated in this manner, with similar spectra, obtained in a similar manner and stored in a conventional library contained in a conventional microprocessor (not shown), yields an identification of material 40, or alternatively, a comparison of the interferogram with similarly obtained interferograms would yield in identification of material 40.

Figure 4:
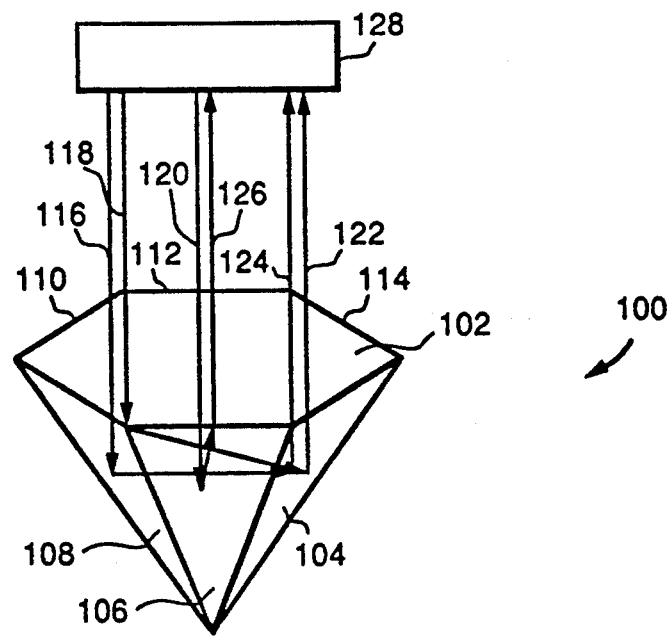
FIG. 4 is another embodiment of a diamond-based, self-sampling internal reflection element, according to the present invention.

With respect to FIG. 4, there is illustrated another embodiment of a diamond-base, self-sampling internal reflection point element 100. Element 100 is constructed of a diamond or diamond-like material, and includes, in part, faces 102, 104, 106, 108, 110, 112, and 114 and detector 128. Detector 128, preferably, is the same as detector 34 (FIGS. 2 and 3). Light beams 116, 118 and 120 from the Fourier transform infrared spectroscope (not shown) are impinged upon element 100 such that light reflects within element 100 and exits element 100 along lines 122, 124 and 126, respectively. The operation of element 100 is the same as the operation of element 20. Namely, element 100 is embedded into sample 40 such that element 100 gets below surface treatment 42 and provides an accurate characterization of material 40. However, element 100 uses a point or very small flat area instead of a knife edge to identify material 40. A point or very small flat area may be advantageous, for example, when there is only a very limited area in material 40 which can be analyzed in order to identify material 40.

Once given the above disclosure, many other features, modification or improvements will become apparent to the skilled artisan. Such features, modifications or improvements are, therefore, considered to be a part of this invention, the scope of which is to be determined by the following claims.

What is claimed is:

1. An apparatus for identifying solid materials, wherein said apparatus is comprised of:
    a solid material to be sampled having first and second sides;
    an optical element means such that said optical element means is embedded substantially in said first side of said material; and
    a detection means which is operatively connected to said optical element means such that said detection means produces a light beam which interacts with said optical element and said material to produce a spectrum of said material that is used to identify said material.

2. The apparatus, as in claim 1,, wherein said material is further comprised of:
    a thermoplastic material.

3. The apparatus, as in claim 1, wherein said optical element means is further comprised of:
    a diamond-like material.

4. The apparatus, as in claim 1, wherein said optical element means is further comprised of:
    a knife.

5. The apparatus, as in claim 1, wherein said optical element means is further comprised of:
    a point.

6. The apparatus, as in claim 1, wherein said optical elements further comprised of:
    first and second sides located a predetermined distance away from each other such that both sides are substantially flat; and
    said second side is substantially smaller in area than said first side.

7. The apparatus, as in claim 1, wherein said detection means is further comprised of:
    a Fourier transform infrared spectrometer.

8. The apparatus, as in claim 1, wherein said detection means is further comprised of:
    a dispersion spectrometer.

9. The apparatus, as in claim 1, wherein said detection means is further comprised of:
    a band-pass infrared detector.

10. The apparatus, as in claim 1, wherein said detection means is further comprised of:
    a light source;
    a spectrometer operatively connected to said light source; and
    a detector operatively connected to said spectrometer.

11. The apparatus, as in claim 1, wherein said detection means is further comprised of:
    a light source;
    a first detector operatively connected to said light source; and
    a second detector operatively connected to said first detector.

12. A method for identifying a solid material using an apparatus comprising a optical element means and detection means, such that said method is comprised of the step of:
    embedding a portion of said optical element means in a first side of said material;
    operating said detection means to produce a light beam;
    impinging said light beam on said element;
    reflecting said light beam substantially within said element such that a portion of said light beam interacts with said material to produce a spectrum of said material;
    directing said light beam and said spectrum out of said element;
    measuring said spectrum in said detection means; and
    comparing said spectrum with a predetermined spectrum to identify said material.

13. The apparatus, as in claim 12, wherein said material is further comprised of:
    a thermoplastic material.

14. The apparatus, as in claim 12, wherein said element means is further comprised of:
    a diamond like material.

15. A method for identifying a solid thermoplastic material, having a surface treatment, using an apparatus which includes an optical element means comprising a diamond-like material and which further includes detection means, said method comprising the steps of:
    (a) penetrating said material below said surface treatment with said optical element means;
    (b) operating said detection means to produce a light beam;
    (c) impinging said light beam on said element;
    (d) reflecting said light beam substantially within said element such that a portion of said light beam interacts with said material to produce a spectrum of said material;
    (e) directing said light beam and said spectrum out of said element;
    (f) measuring said spectrum in said detection means; and
    (g) comparing said spectrum with a predetermined spectrum to identify said material.

16. The method of claim 15, wherein said surface treatment includes a textured area and wherein the step of penetrating said material includes penetrating said material below said textured area.

17. The method of claim 15, wherein said surface treatment includes a painted coating and wherein the step of penetrating said material includes penetrating said material below said painted coating.

18. The method of claim 15, wherein said surface treatment includes a metallized coating and wherein the step of penetrating said material includes penetrating said material below said metallized coating.

19. The method of claim 15, wherein said element includes a knife edge and wherein said step of penetrating said material with said element includes plowing through said material with said knife edge.

20. The method of claim 15, wherein said element includes a point and wherein said step of penetrating said material with said element includes puncturing said material with said point.

* * * * *